(12) United States Patent
Rumphorst et al.

(10) Patent No.: US 6,281,271 B1
(45) Date of Patent: Aug. 28, 2001

(54) RADICALLY POLYMERIZABLE DENTAL MATERIAL

(75) Inventors: André Rumphorst, Vaduz; Ulrich Salz, Lindau; Alexandros Gianasmidis, Heerbrugg; Thomas Völkel, Lindau; Volker Rheinberger, Vaduz; Norbert Moszner, Eschen, all of (DE)

(73) Assignee: Ivoclar AG (LI)

( * ) Notice: Subject to any disclaimer, the term of this patent is extended or adjusted under 35 U.S.C. 154(b) by 0 days.

(21) Appl. No.: 09/296,340

(22) Filed: Apr. 22, 1999

(30) Foreign Application Priority Data

Apr. 24, 1998 (DE) .............................................. 198 18 210

(51) Int. Cl.$^7$ .............................. A61K 6/083; C08K 9/04; C08K 3/34; C08K 3/36; C08K 3/40
(52) U.S. Cl. .......................... 523/211; 523/116; 523/117; 523/118; 522/71; 522/83; 524/786; 524/789; 524/790; 524/853
(58) Field of Search ........................ 522/71, 83; 523/211, 523/116, 117, 118; 524/786, 789, 790, 853

(56) References Cited

U.S. PATENT DOCUMENTS

| | | | | |
|---|---|---|---|---|
| 3,940,362 | * | 2/1976 | Overhults .............................. | 523/116 |
| 3,991,008 | | 11/1976 | Temin et al. .......................... | 523/116 |
| 5,154,762 | | 10/1992 | Mitra et al. ........................... | 523/116 |
| 5,367,002 | | 11/1994 | Huang et al. ......................... | 523/116 |
| 5,554,665 | | 9/1996 | Tateosian et al. ..................... | 522/30 |
| 5,710,194 | | 1/1998 | Hammesfahr et al. .............. | 523/116 |

OTHER PUBLICATIONS

Hickel, "Moderne Füllungswerkstoffe," *Stomatologie*, 94/7:363–382 (1997).

Misra et al., "Redox Polymerization," *Proc. Polym. Sci.*, 8:61–131 (1982).

Dietliker, "Photoinitiators for Pigmented Systems," in Foyuassier, eds., *Radiation Curing in Polymer Science and Technology—Volume II* London: Elsevier Applied Science, pp. 155–237 (1993).

Carlini et al., "Polymeric Photoinitiators," in Fouassier, eds., *Radiation Curing in Polymer Science and Technology—Volume II* London: Elsevier Applied Science, pp. 283–321 (1993).

Cunningham et al., "Metal–Based Photoinitiators," in Fouassier, eds., *Radiation Curing in Polymer Science and Technology—Volume II* London: Elsevier Applied Science, pp. 324–373 (1993).

Green et al., "Water–Soluable Photoinitiators," in Fouassier, eds., *Radiation Curing in Polymer Science and Technology—Volume II* London: Elsevier Applied Science, pp. 375–434 (1993).

\* cited by examiner

*Primary Examiner*—Peter Szekely
(74) *Attorney, Agent, or Firm*—Nixon Peabody LLP

(57) ABSTRACT

The invention relates to a dental material with at least one polymerizable binder and at least one filler containing a redox-initiator system for the radical polymerization, which comprises an initiator and an activator. The material is characterized in that the filler contains a homogeneous mixture of a first part of the filler, which is mixed with the initiator, a second part of the filler, which is mixed with the activator, and a third part of the filler, which does not contain a component of the initiator system. The materials are particularly suitable as cements and filling materials.

22 Claims, No Drawings

RADICALLY POLYMERIZABLE DENTAL MATERIAL

The invention relates to two- and multi-component, radically polymerizable dental materials which are particularly suitable as cements and filling materials.

Cements and filling materials can be divided roughly into glass ionomer cements and composites (cf. for example R. Hickel, Stomatologie (1997) 94/7:363–382). Glass ionomer cements are aqueous, two-component cements based on polymeric organic acids such as for example poly(acrylic acid) and powdery solid bases such as calcium-fluorine-aluminium silicate glasses. The cement is cured by ionic reaction between polymer-bonded carboxyl groups and calcium or aluminium ions emerging from the filler. Glass ionomer cements are characterized by a high fluoride release which reduces the danger of secondary caries, but are not suitable for occlusion-bearing fillings because of their poor flexural strength.

The term composites describes compositions which consist essentially of a polymerizable binder and an organic or inorganic filler. Composites have a clearly higher flexural strength than glass ionomer cements, but do not generally release fluoride ions and also require the use of dentive adhesives and completely dry conditions during application.

Recently, it has been attempted to combine the positive properties of glass ionomer cements and composites. To do this, aqueous, plastics-modified glass ionomer cements (hybrid ionomers) and anhydrous compomers were suggested, whose curing is based on both an acid-base reaction and a radical polymerization.

The curing of composites, hybrid ionomers and compomers generally comprises a radical polymerization which is initiated chemically, by light or heat. Light- or heat-curing has the advantage that the materials remain processable up to irradiation with a suitable light source, and can as a rule be preserved over long periods of time when stored in opaque containers. The use of photoinitiators is however restricted to light-permeable materials and for deep cavities, a step-by-step processing and curing is necessary. In addition, the use of photopolymerizable materials is restricted to areas which are accessible for the polymerization lamp. Heat-curable materials cannot be used in the patient's mouth.

Chemical curing is carried out by using redox systems as polymerization initiators. These have the advantage that they can also be used with opaque materials and deep cavities. However, their restricted storage stability is disadvantageous.

Redox-initiator systems for chemical polymerization contain initiators such as peroxide or azo-compounds which can form free radicals (oxidizing substance) and a reducing substance which serves as an activator. The polymerization is triggered by mixing initiator and activator.

U.S. Pat. No. 3,991,008 discloses polymerizable dental materials with improved colour and storage stability, which contain substituted thiourea derivatives as reducing agents.

U.S. Pat. No. 5,554,665 describes the use of oxygen-permeable containers for storing chemically curable dental materials. The polymerization of the components is said to be inhibited by the incoming atmospheric oxygen.

U.S. Pat. No. 5,367,002 discloses dental materials which contain a curable liquid composition and a powdery component. The curing of the materials takes place on the one hand by the ionic reaction of polyalkene acids with an ion-releasing filler and on the other hand by radical polymerization. The materials can contain a redox-initiator system, the constituents of the redox system being distributed over different components of the dental material. Because of hydrolytic and/or undesired redox reactions in the liquid phase, the systems have a limited durability only. The use of strongly acidic monomers is not possible due to possible reactions with the constituents of the redox system.

According to U.S. Pat. No. 5,154,762, the constituents of the redox system are microencapsulated so that both components can be worked into the solid phase. In this way, reactions in the liquid phase can be avoided and the durability of the materials increased. However, to initiate the polymerization, initiator and activator must be released by dissolving the microcapsules or by their mechanical destruction. This requires either a relatively long activation period or the use of strong mechanical forces. In addition, microencapsulation is a laborious and thus cost-intensive process.

The object of the present invention is the preparation of a two- or multi-component dental material polymerizable at room temperature, in which the constituents of the redox-initiator system are contained in a single solid component, which can be manufactured easily and is polymerizable without the disadvantages described.

The object is achieved by dental materials with at least one polymerizable binder and at least one filler, the material containing a redox-initiator system for the radical polymerization, which comprises an initiator and an activator. The dental material is characterized in that the filler contains a homogeneous mixture of a first part of the filler, which is mixed with the initiator, a second part of the filler, which is mixed with the activator, and a third part of the filler, which does not contain a component of the initiator system.

With the dental materials according to the invention, the third filler portion functions as a thinner for the two initiator- or activator-containing filler portions so that, during conventional storage of the filler, no reaction takes place between initiator and activator. When the filler is mixed with the binder, the constituents of the redox-initiator system are dissolved by the binder and the redox-reaction initiated. By mixing initiator and activator with a part of the filler each, a uniform distribution of the constituents and thus a uniform polymerization of the dental material is ensured.

The filler preferably contains 20 to 90 wt.-%, particularly preferably 50 to 90 wt.-% and most preferably 70 to 90 wt.-% of the third filler part. The first and second filler parts are preferably used in the same amount.

The initiator is preferably mixed with the filler in a ratio such that the first filler part contains 1 to 20 wt.-%, preferably 7 to 15 wt.-% of the initiator, relative to the sum of the masses of initiator and filler. Similarly, the activator is preferably mixed with the filler in a ratio such that the second filler part contains 1 to 20 wt.-%, preferably 7 to 15 wt.-% of the activator, relative to the sum of the masses of activator and filler.

The ratio of the individual filler parts is selected such that the amount of each redox component is preferably 0.01 to 10 wt.-%, particularly preferably 0.02 to 5 wt.-%, quite particularly preferably 0.1 to 5 wt.-%, relative to the overall mass of the filler. The most preferred ranges are 0.2 to 1 wt.-%, and in particular 0.5 to 1 wt.-% relative to the overall mass of the filler.

Suitable redox-initiator systems are described in "Redox Polymerization", G. S. Misra and U. D. N. Bajpai, Proc. Polym. Sci., 8, 61–131 (1982).

Preferred initiators (oxidizing substances) are cobalt(III) chloride, tert.-butyl hydroperoxide, iron(III) chloride, hydroxylamine (depending on the activator selected), perboric acid and its salts, and salts of permanganate anions or per-sulphate anions. Hydrogen peroxide can also be used, although if a photoinitiator is used simultaneously, interactions can take place.

Preferred activators (reducing substances) are ascorbic acid, cobalt(II) chloride, iron(II) chloride, iron(II) sulphate, hydrazine, hydroxylamine (depending on the initiator selected), oxalic acid, thiourea and salts of dithionite or sulphite anions.

Particularly preferred activators are ascorbic acid and benzyl-phenyl barbituric acid (BPBS), particularly preferred initiators are benzoyl peroxide (BPO) and lauroyl peroxide. The most preferred redox system is BPO/BPBS.

Besides the redox initiator, the dental materials according to the invention can additionally contain one or more photoinitiators. Preferred photoinitiators are benzoin ether, dialkylbenzil ketales, dialkoxyacetophenones, acylphosphinoxides, α-diketones, such as 9,10-phenanthrenequinone, diacetyl, furil, anisil, 4,4'-dichlorobenzil and 4,4'-dialkoxybenzil and in particular camphor quinone (cf. J. P. Fouassier, J. F. Rabek (publishers), Radiation Curing in Polymer Science and Technology, Vol II, Elsevier Applied Science, London, N.Y. 1993).

Preferred fillers are quartz, glass ceramic or glass powders, as well as aluminium- and silicon oxide powder, in particular silicate glasses such as barium silicate glasses, Li/Al silicate glasses, Ba/Al silicate glasses and barium glasses as well as mixtures thereof. Particularly preferred fillers are ion-releasing glasses, in particular ion-releasing Ba/Al silicate glasses.

The fillers are used as powder with a particle size of preferably 0.1 to 50 μm, in particular 1 to 20 μm.

In addition, the filler can also contain pigments, X-ray opacity agents, preferably ytterbium trifluoride, thixotropic agents such as pyrogenic and/or precipitated silicas, accelerators, for example metal salts and complex compounds such as copper acetate, copper acetyl acetonate, copper salicylate, Co-EDTA complex and further auxiliaries and additives. Silicas are normally used in a quantity of up to 20 wt.-%, preferably 1 to 10 wt.-%.

A preferred filler mixture contains 40 to 90 wt.-% of at least one of the above-mentioned preferred fillers, 0 to 50 wt.-% X-ray opacity agent and 0 to 10 wt.-% thixotropic agent relative to the overall mass of filler.

A particularly preferred filler contains 60 to 80 wt.-% silicate glass, 20 to 40 wt.-% ytterbium trifluoride and 1 to 5 wt.-% precipitation silica. The mixture preferably also contains 0.2 to 1 wt.-% benzoyl peroxide and 0.2 to 1 wt.-% benzylphenyl barbituric acid.

The components of the redox-initiator system and of the filler are preferably mixed by coating filler particles with the initiator or activator, for example by suspending the filler in a solution of the initiator or activator and then removing the solvent. The filler can then be optionally dried. Subsequently, the different filler portions are mixed together and optionally further dry auxiliaries and fillers are added. The filler thus obtained can be packed and stored.

The fillers are preferably silanized. To do this, customary, commercially available silanization agents such as vinyl triethoxysilane, vinyl trimethoxysilane, vinyl tris(beta-methoxyethoxy)silane, gamma-methacryloxypropyl-trimethoxysilane(silane A-174), gamma-methacryloxypropyl-tris(2-methoxyethoxy)silane, gamma-glycidoxypropyltrimethoxysilane, vinyltriacetoxysilane, gamma-mercaptopropyltrimethoxysilane, gamma-aminopropyltriethoxy-silane, N-beta-(aminoethyl)-gamma-aminopropyltrimethoxysilane (Union Carbide) can be used. Silanes without amino and mercapto groups are preferred, silane A-174 particularly preferred.

A particular advantage of the filler according to the invention is that it contains oxidizing and reducing substances in a pre-set proportion and that these components need not be mixed together by the user prior to use. The fillers are easy to manufacture, are not subject to hydrolysis and show a surprisingly high storage stability.

The additives and auxiliaries and the photoinitiator can either directly be added to the mixture of the three obligatory filler parts or alternatively first mixed with a small amount of the filler and then combined with the rest of the filler. The auxiliaries can also be coated as described onto filler particles. Alternatively, the auxiliaries and the photoinitiator can also be added to the binder.

The components of the redox-initiator system and optionally the auxiliaries and additives can be coated onto different components of the filler. Alternatively, the different filler components can be combined and the mixture then divided up into several portions which are then coated with the components of the redox-initiator system and optionally with the additives and auxiliaries, and then combined again.

The binder contains at least one polymerizable monomer, oligomer, prepolymer and/or macromonomer. The term macromers describes short polymers with a terminal group capable of polymerization. Oligomers are built up from at least 5, normally 50 to 300 monomer components. Oligomers and polymers with polymerizable groups are covered by the term prepolymer.

Monomers suitable according to the invention are described in the U.S. Pat. No. 5,554,665, column 6 to column 8. Preferred monomers are methyl methacrylate, isobutyl methacrylate, butoxymethyl methacrylate, 2-ethylhexyl methacrylate, isodecyl methacrylate, phenoxyethyl methacrylate, ethyl methacrylate, butyl methacrylate, benzyl methacrylate, phenyl methacrylate, tetra-hyrdofurfuryl methacrylate, 1,4-butanediol dimethacrylate, 1,6-hexanediol dimethacrylate, 1,9-nonanediol dimethylacrylate, trimethylolpropane trimethacrylate, pentaerythritol tetramethacrylate, dipentaerythritol pentamethacrylate, bis-[4-methacryloxy-2-hydroxypropyloxyphenyl] propane, polyethylene glycol methacrylate, for example on the basis of polyethylene glycol (PEG) 300, 400 or 1,000, bisphenol-A-dimethacrylate and in particular ethylene glycol dimethacrylate, triethylene glycol dimethacrylate, dipropylene glycol dimethacrylate, bis-GMA (2,2-bis-4-(3-methacryloxy-2-hydroxypropyl)-phenyl propane), 1,1,6-trimethyl hexamethylene urethane dimethacrylate, cyclohexyl methacrylate, urethane dimethacrylate (UDMA, reaction product of hydroxyethyl(meth)acrylate or hydroxypropyl(meth)acrylate with 2,2,4-trimethylhexyl-1, 6-diisocyanate), hydroxyethyl methacrylate (HEMA), glycerine mono-, -di- and -trimethacrylate. Hydroxyethyl methacrylate and glycerine dimethacrylate (GDMA) are preferred.

Acid oligomers which contain carboxylate groups as well as methacrylate groups, are preferred oligomers, statistical oligomers based on acrylic acids and glycidyl methacrylate being quite particularly preferred.

Oligomers based on acrylic acid and glycidyl methacrylate are preferably obtained by first partially polymerizing acrylic acid with a radical transfer agent in a solvent with an initiator for the radical polymerization, i.e. converting it into oligomers with 5 to 40 monomer units. N mol acrylic acid are preferably used per mol of radical transfer agent, the number n preferably being 5 to 40, particularly preferably 5 to 20 and most preferably 8 to 12.

Polar organic solvents with a boiling point of over 50° C. are preferably used as solvents. Alcohols such as ethanol, propanol and butanol and particularly sec.-butanol are preferred.

Peroxides, chloroform, azo compounds such as for example azoisobutyronitrile, and particularly mercaptanes, very particularly 2-mercaptoethanol are suitable as radical transfer agents.

Preferred initiators are azo compounds such as azoisobutyronitrile and particularly azobiscyanovaleric acid.

The reaction temperature can fluctuate within broad limits and lies preferably in the range from 50 to 120° C., in particular 80 to 100° C.

As an intermediate product, an oligomeric acrylic acid is obtained whose end groups are determined by the radical transfer agent used. The use of 2-mercaptoethanol results for example in compounds with 2-hydroxyethylthio end groups according to the formula

$H-[-CH_2-CH(COOH)]_n-S-(CH_2)_2OH$, n having the above-stated meaning.

The intermediate product is expediently reacted under normal pressure with an m-fold, preferably 3- to 40-fold, particularly preferably 3- to 20-fold and most preferably 3 to 7-fold molar excess of glycidyl methacrylate at 40 to 90° C., preferably 50 to 70° C. As a rule, the product from the first stage can be used directly in the second stage without further processing. The end product is generally obtained after the solvent has been removed. The reaction sequence leads to statistical oligomers with a molecular weight of 1,000 to approx. 30,000, preferably 1,200 to 10,000, particularly preferably 1,200 to 5,000. The molecular weight of the statistical oligomers depends on the chain length of the intermediate product. Approximately half of the carboxylic acid groups are esterified.

The product obtained when using 2-mercaptoethanol as radical transfer agent can be described approximately by the formula

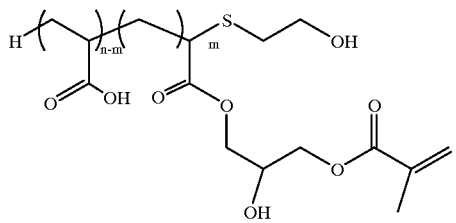

the $-COOH$ and $-COOCH_2-CH(OH)-CH_2-O-CO-(CH_3)=CH_2$ groups being statistically distributed in the chain of n units.

Preferred prepolymers are disclosed in WO 96/09332. These are block copolymers from polymerizable oligo- and/or polyalkene acids of the general formula $A-[B_x-C_y-D_z-]_n-E$, in which the groups A and E are the same or differently hydrogen, halogen atoms, methacrylate, acrylate, allyl, vinyl, alkyl, aryl, alkoxy, aryloxy, carboxyl, amine, hydroxy, isocyanate, silyl and/or siloxy groups, and function as end groups.

The oligomer/polymer is composed of at least two blocks (here=groups) of sequences, the one group B being a segment composed of sequences of mono-, di- and/or tricarboxylic acids as monomer components, their anhydrides, salts and/or derivatives of these acids, with an acid protection group known per se from which the acid is to be easily released. The other group C is composed of sequences of mono-, di- and/or tricarboxylic acid esters and/or their amides as well as isoprene and/or butadiene components as monomer components, the alcohol components of the esters and the amine component of the amides each being saturated.

A third optional group D consists of sequences of mono-, di- and/or tricarboxylic acids as monomer components, their esters, amides and/or nitrites which contain no double bonds.

The order of the groups B, C and D within the blocks $[-B_x-C_y-D_z-]$ is as wished and can be different for each n.

The monomer components contained in the groups B, C and D in sequential order are the same in each case for a particular n, but can be different for different values of n.

The indices stand for n=1 to 10, x, y, z=0 or 4 to 1,000, x being at least 4 and y at least 4 for at least one n, and x, y, z may be different for each n. Preferably, n=1 to 4, x and y at least 4 and z=0 or at least also 4. Preferred prepolymers are those with the formula:

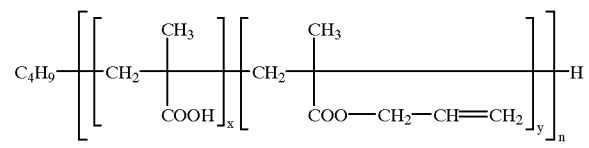

mit x = 180–200, y = 80–100; n = 1

The binder is preferably liquid, particularly preferably thinly liquid. To guarantee a sufficient flowability and to facilitate mixing with the filler, the binder can contain a solvent. Preferred solvents are alcohols, in particular ethanol, water or their mixtures. In addition, liquid monomers can serve as solvents. The most preferred solvent is water. The solvent content is selected so that the binder has the desired viscosity. Normally, the proportion of solvent is 0 to 80 wt.-%, particularly preferably 10 to 40 wt.-%.

The binders preferably contain a mixture of at least one monomer and at least one oligomer, prepolymer and/or macromonomer.

Preferred binders contain 5 to 80 wt.-% monomer, 1 to 40 wt.-% oligomer, prepolymer or macromonomer and 10 to 40 wt.-% solvent relative to the overall mass of the binder.

A particularly preferred binder contains 10 to 40 wt.-% hydroxyethyl methacrylate, 10 to 40 wt.-% glycerine dimethacrylate, 10 to 40 wt.-% of a statistical oligomer based on acrylic acid, 2-mercaptoethanol and glycidyl methacrylate and 10 to 30 wt.-% water.

According to the invention, particularly preferred dental materials are those which contain one or more ion-releasing fillers in addition to a polymerizable binder with organic acid groups. The curing of these dental materials takes place on the one hand by an acid-base reaction between binder and filler and on the other hand by radical polymerization of the binder. The ionic reaction is promoted by the use of water as a solvent.

For dental cements, binder and filler are preferably mixed in a ratio of 1.5:1 to 3:1, particularly preferably 2:1 to 2.5:1. For fillers, the ratio of binder to filler is preferably 0.5:1 to 1,5:1.

The components are mixed shortly before use. As a rule, the processing time is 1 to 5 minutes, preferably 2 to 3 minutes.

The dental materials can be used in transparent or coloured form.

In the following, the invention is explained using embodiments.

EXAMPLE 1

Synthesis of a Statistical Oligomer Based on Acrylic Acid, 2-Mercaptoethanol and Glycidyl Methacrylate 350 ml sec.-butanol were mixed simultaneously over a period of 60 minutes at 95° C. accompanied by vigorous stirring with 288.8 g (4 mol) of acrylic acid and a solution of 31.2 g (0.4 mol) mercaptoethanol and 5.6 g (20 mmol) azobiscyanovaleric acid in 250 ml sec. butanol. To guarantee the complete decomposition of the initiator, the mixture was subsequently stirred for 16 hours at 90° C. The intermediate product can be described by the formula

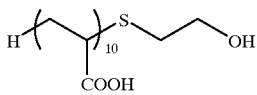

$^1$H-NMR (CDCl$_3$/DMSO-D$_6$): δ=1.49–1.61 (br, CH$_2$, $_{main\ chain}$), 2.15–2.62 (br, Ch$_{main\ chain}$), 2.71 (t, CH$_2$S), 3.71 (t, CH$_2$O) and 11.97 (br, acid) ppm.

IR (film): 3580–2400 (s and br), 2956 (s), 1709 (s), 1411 (m) and 1238 cm$^{-1}$.

Afterwards, the reaction mixture was mixed without further purification with 227.4 g (1.6 mol) GMA and 80 mg hydroquinone-monomethyl ether (MeHQ) as stabilizer and stirred for 2 days at 60° C. The decrease in the GMA concentration was tracked by means of HPLC. During the reaction, 50% of the carboxylic acid residue were reacted with glycidyl methacrylate. The molecular weight of the oligomer obtained was approximately 1,500. The product can be described approximately by the formula

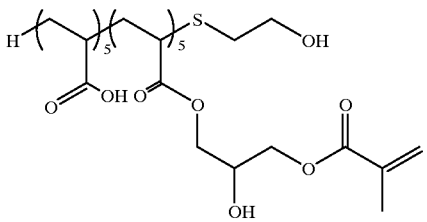

the distribution of the —COOH and —COOCH$_2$—CH(OH)—CH$_2$—O—CO—C(CH$_3$)=CH$_2$ groups in the chain of 10 units being statistical.

$^1$H-NMR (CDCl$_3$/DMSO-D$_6$): δ=1.43–1.68 (br, CH$_2$, $_{main\ chain}$), 1.93 (s, CH$_3$), 2.15–2.58 (br, Ch$_{main\ chain}$), 2.76 (t, CH$_2$S), 3.70–4.40 (br, CH0 and CH$_2$O), 5.64 and 6.15 (2 s, =CH$_2$) and 12.18 (br, acid) ppm.

IR (cap.): 3500–2400 (s and br), 2960 (s), 1712 (s), 1635 (m), 1453 (m), 1298 (s) and 1161 (s) cm$^{-1}$.

Afterwards, the mixture was mixed with 600 g HEMA and the solvent removed by introducing air under vacuum (180 mbar) at a maximum 55° C. at the rotary evaporator.

EXAMPLE 2

Preparation of a Dental Material

1. Binder
A mixture of the following components is prepared:
19.8 wt.-% water (deionized)
27.9 wt.-% hydroxyethyl methacrylate (HEMA)
27.6 wt.-% glycerine-1,3-dimethacrylate (GDMA)
24.7 wt.-% oligomer from example 1 (dissolved in HEMA, the HEMA portion is already contained in the 27.9 wt.-%)

2. Filler 2.1 Silanization of the Filler 95.24 wt.-% of a fluorine-calcium-aluminium-silicate glass powder (23.1 wt.-% SiO$_2$; 21.6 wt.-% Al$_2$O$_3$; 16.4.wt.-% CaO; 8.7 wt.-% P$_2$O$_5$; 1.9 wt.-% Na$_2$O; 11.2 wt.-% BaO; 17.1 wt.-% F; ionomer glass SP-2034, Speciality Glass) with an average particle size of 7 μm were wetted uniformly in a suitable container with 1.90 wt.-% deionized water and then homogenized well for 15 minutes. Afterwards, the mixture was mixed carefully with 2.86 wt.-% gamma-methacryloxypropyl-trimethoxy-silane (silane A-174, Union Carbide), homogenized again for 15 minutes and then left to stand in a closed container for 24 hours. When adding the water or silane, as uniform as possible a distribution is to prevent lumps from forming.

The silanized ionomer glass is screened through a sieve with a mesh width of 125 μm, dried at 50° C. and then screened through a sieve with a mesh width of 90 μm.

2.2 Coating the Filler with Initiator

In a metal-free container, 2.13 wt.-% benzoylperoxide (BPO, 76% moistened with 24 wt.-% water) were dissolved in 81.56 wt.-% of acetic acid ethyl ester, accompanied by stirring with a metal-free stirrer. 16.31 wt.-% of the silanized ionomer glass were then added and suspended in the solution. Afterwards, the solvent was evaporated, accompanied by vigorous stirring of the suspension in vacuo until dry. The evaporation of the solvent should be carried out as slowly as possible in order to coat the glass particles evenly with the BPO. The cake of coated powder was broken up and comminuted carefully by hand. After drying in vacuo, the powder obtained was screened through a nylon sieve with a mesh width of 90 μm.

2.3 Coating the Filler with Activator 1.64 wt.-% benzylphenyl barbituric acid (BPBS) were dissolved in a metal-free container with a non-metal stirrer in 81.97 wt.-% acetic acid ethyl ester. 16.39 wt.-% of the silanized ionomer glass powder were then added and suspended in the solution. Afterwards, the solvent was evaporated until dry accompanied by vigorous stirring of the suspension, in vacuo. The evaporation of the solvent should take place as slowly as possible in order to coat the surface of the glass particles evenly with the benzylphenyl barbituric acid. The cake of coated powder was broken up and comminuted carefully by hand. After drying in vacuo, the powder was screened through a nylon sieve with a mesh width of 90 μm.

2.4 Mixing the Filler Portions

A homogenous mixture of the following components was prepared in a Rhönrad mixer (Engelsmann), during cooling at a temperature of no more than 30° C.,:

59.0 wt.-% silanized ionomer glass
8.0 wt.-% benzoyl peroxide-coated ionomer glass
6.0 wt.-% benzylphenyl barbituric acid-coated ionomer glass
25.0 wt.-% YbF$_3$ (Rhone Poulenc)
2.00 wt.-% highly-dispersed silica with a BET surface of 392 m$^2$/g (HDK T 40, Wacker)

3. Combining of Binder and Filler

Binder and filler were mixed with a spatula in a weight ratio of 1:2.25 on a glass plate.

After curing, the dental material showed the following physical properties:

Modulus of elasticity[1]: 3300–3800 Mpa

Flexural strength[1] 40–50 Mpa

Processing time: 120" 30 sec at 23° C.

Curing time: 360–420 sec at 23° C.

Expansion[2] 0.4%

[1] Measured according to ISO standard 4049 (1988) after the times given above
[2] After 4-week storage in 0.8% NaCl solution at 37° C.

With good flexural strength and a satisfactory E-modulus, the materials are characterized by a particularly small expansion after several weeks' storage in water.

What is claimed is:

1. A polymerizable dental material comprising:

a polymerizable binder as a first component and a filler comprising a homogenous mixture of at least three filler portions as a second component, the filler containing a redox-initiator system for radical polymerization, which includes an initiator and an activator, wherein the initiator is mixed with a first portion of the filler, the activator is mixed with a second portion of the filler, and the first and second portion of the filler are mixed with a third portion of the filler, which does not contain initiator or activator.

2. A polymerizable dental material according to claim 1, wherein the proportion of the third filler part is 20 to 90 wt.-% of the overall mass of the at least one filler.

3. A polymerizable dental material according to claim 1, wherein the first filler part contains 1 to 20 wt.-% of the initiator, and/or the second filler part contains 1 to 20 wt.-% of the activator, in each case, relative to the sum of the masses of initiator or activator and the at least one filler.

4. A polymerizable dental material according to claim 1, wherein the at least one filler contains 0.01 to 10 wt.-% each of initiator or activator, relative to the overall mass of the at least one filler.

5. A polymerizable dental material according to claim 1, wherein the initiator is benzoyl peroxide, lauroyl peroxide, or a combination thereof.

6. A polymerizable dental material according to claim 1, wherein the activator is ascorbic acid, benzylphenyl barbituric acid, or a combination thereof.

7. A polymerizable dental material according to claim 1, further comprising a photoinitiator.

8. A polymerizable dental material according to claim 1, wherein the at least one filler is selected from the group consisting of quartz powder, glass ceramic powder, glass powder, aluminium powder, silicon oxide powder, and a combination thereof.

9. A polymerizable dental material according to claim 8, wherein the at least one filler comprises at least one silicate glass.

10. A polymerizable dental material according to claim 9, wherein the at least one silicate glass is selected from the group consisting of barium glass powder, barium silicate glass powder, Li/Al silicate glass powder, Ba/Al silicate glass powder, and a combination thereof.

11. A polymerizable dental material according to claim 8 further comprising pigments, X-ray opacity agents, thixotropic agents, accelerators, or combinations thereof.

12. A polymerizable dental material according to claim 11, wherein the at least one filler comprises 60 to 80 wt.-% silicate glass, 20 to 40 wt.-% ytterbium trifluoride, and 1 to 5 wt.-% precipitation silica, relative to the overall mass of the filler.

13. A dental material according to claim 12, wherein the at least one filler comprises 0.2 to 1 wt.-% benzoyl peroxide and 0.2 to 1 wt.-% benzylphenyl barbituric acid.

14. A polymerizable dental material according to claim 1, wherein the at least one binder contains a component selected from the group consisting of methyl methacrylate, isobutyl methacrylate, butoxymethyl methacrylate, 2-ethylhexyl methacrylate, isodecyl methacrylate, phenoxyethyl methacrylate, ethyl methacrylate, butyl methacrylate, benzyl methacrylate, phenyl methacrylate, tetrahydrofurfuryl methacrylate, 1,4-butanediol dimethacrylate, 1,6-hexanediol dimethacrylate, 1,9-nonanediol dimethacrylate, trimethylolpropane trimethacrylate, pentaerythritol tetramethacrylate, dipentaerythritol pentamethacrylate, bis-(4-methacryloxy-2-hydroxypropyloxyphenyl) propane, polyethylene glycol methacrylate, bisphenol-A-dimethacrylate, ethylene glycol dimethacrylate, triethylene glycol dimethacrylate, dipropylene glycol dimethacrylate, bis-GMA(2,2-bis-4-(3-methacryloxy-2-hydroxypropyl)-phenyl propane), 1,1,6-trimethylhexamethylene urethane di-methacrylate, cyclohexyl methacrylate, urethane dimethacrylate (UDMA, reaction product of hydroxyethyl(meth)acrylate or hydroxypropyl-(meth)-acrylate with 2,2,4-trimethylhexyl-1,6-diisocyanate), hydroxyethyl methacrylate (HEMA), glycerine mono-, -di-(GDMA) and -trimethacrylate, hydroxyethyl methacrylate, glycerine dimethacrylate, an acidic, polymerizable oligomer, an acidic, polymerizable block copolymer, and a combination thereof.

15. A polymerizable dental material according to claim 14, wherein the at least one binder comprises hydroxyethyl methacrylate, glycerine dimethacrylate, a statistical oligomer based on acrylic acid, 2-mercaptoethanol, glycidyl methacrylate, or mixtures thereof.

16. A polymerizable dental material according to claim 1, wherein the at least one binder is a liquid.

17. A polymerizable dental material according to claim 16, wherein the at least one binder further comprises a solvent.

18. A polymerizable dental material according to claim 17, wherein the at least one binder further comprises water.

19. A polymerizable dental material according to claim 18, wherein the at least one binder comprises 10 to 40 wt.-% hydroxyethyl methacrylate, 10 to 40 wt.-% glycerine dimethacrylate, 10 to 40 wt.-% of a statistical oligomer based on acrylic acid, 2-mercaptoethanol and glycidyl methacrylate and 10 to 30 wt.-% water, relative to the overall mass of the binder.

20. A dental cement comprising a polymerizable dental material according to claim 1.

21. A dental filling comprising a polymerizable dental material according to claim 1.

22. A polymerizable dental material comprising:

a first component comprising a polymerizable binder and a second component comprising a filler containing a redox-initiator system for radical polymerization, which includes an initiator and an activator, said filler comprising a homogenous mixture of at least three filler portions, wherein a first portion comprises filler mixed with the initiator, a second portion comprises filler mixed with the activator, and a third portion comprises filler which does not contain the initiator or activator.

* * * * *